(12) United States Patent
Allen et al.

(10) Patent No.: US 7,002,054 B2
(45) Date of Patent: Feb. 21, 2006

(54) ABSORBENT ARTICLE HAVING A FEVER INDICATOR

(75) Inventors: Patrick Jay Allen, Cincinnati, OH (US); Donald Carroll Roe, West Chester, OH (US); Oliver Edwin Clarke Mason, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 452 days.

(21) Appl. No.: 10/078,826

(22) Filed: Feb. 19, 2002

(65) Prior Publication Data

US 2003/0014025 A1    Jan. 16, 2003

Related U.S. Application Data

(60) Provisional application No. 60/302,481, filed on Jun. 29, 2001.

(51) Int. Cl.
*A61F 13/15* (2006.01)

(52) U.S. Cl. ............... 604/361; 604/364; 604/362; 600/549; 374/160; 374/162; 116/217

(58) Field of Classification Search ............... 604/364, 604/361, 362; 600/549; 116/218, 106, 217, 116/219, 208; 374/160, 162
See application file for complete search history.

(56) References Cited

U.S. PATENT DOCUMENTS

| | | | |
|---|---|---|---|
| 3,998,098 A | 12/1976 | Chilton | |
| 4,232,552 A | 11/1980 | Hof et al. | |
| 4,345,470 A | 8/1982 | Hof et al. | |
| 4,408,905 A | 10/1983 | Ehrenkranz | |
| 4,457,253 A | 7/1984 | Manske | |
| 4,564,299 A | 1/1986 | Ehrenkranz | |
| 5,094,545 A * | 3/1992 | Larsson et al. | 374/160 |
| 5,174,656 A | 12/1992 | Dotan | |
| 5,197,958 A * | 3/1993 | Howell | 604/361 |
| 5,222,809 A * | 6/1993 | Ehrenkranz | 374/141 |
| 5,232,552 A | 8/1993 | Lundberg et al. | |
| 5,291,181 A | 3/1994 | DePonte | |
| 5,389,093 A | 2/1995 | Howell | |
| 5,416,469 A | 5/1995 | Colling | |
| 5,468,236 A | 11/1995 | Everhart et al. | |
| 5,649,914 A * | 7/1997 | Glaug et al. | 604/361 |
| 5,713,881 A * | 2/1998 | Rezai et al. | 604/368 |
| 5,790,035 A | 8/1998 | Ho | |
| 5,802,611 A * | 9/1998 | McKenzie et al. | 2/69 |
| 6,342,037 B1 | 1/2002 | Roe et al. | |
| 6,541,517 B1 * | 4/2003 | Murphy et al. | 514/547 |

FOREIGN PATENT DOCUMENTS

| | | |
|---|---|---|
| WO | WO 00/00148 A1 | 1/2000 |
| WO | WO 00/00233 A1 | 1/2000 |
| WO | WO 00/65348 A2 | 11/2000 |
| WO | WO 01/54552 A1 | 8/2001 |
| WO | WO 01/65263 A2 | 9/2001 |

\* cited by examiner

*Primary Examiner*—Jacqueline F. Stephens
(74) *Attorney, Agent, or Firm*—Michael P. Hayden; Matthew P. Fitzpatrick; Ken K. Patel (57) ABSTRACT

A wearable article including a fever indicator disposed on at least a portion of the article for indicating the body temperature of a wearer. The fever indicator may be used in conjunction with a disposable absorbent article and provides a signal indicating qualitative or quantitative information about the body temperature of the wearer based on the temperature of the wearer's urine.

18 Claims, 4 Drawing Sheets

ABSORBENT ARTICLE HAVING A FEVER INDICATOR

CROSS-REFERENCE TO RELATED APPLICATION

Applicants hereby claim the benefit of U.S. Provisional Application Ser. No. 60/302,481, Confirmation No. 7838, filed on 29 Jun. 2001 in the name of Allen et al., in accordance with 35 U.S.C. 119(e).

FIELD OF THE INVENTION

This invention is directed to a fever indicator that may be used in conjunction with a wearable article. More particularly, the invention relates to hygienic absorbent articles, such as diapers, adult incontinence articles, feminine protection articles and the like including a fever indicator.

BACKGROUND OF THE INVENTION

Wearable and absorbent articles are well known in the art. Absorbent articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, most of these articles are not adapted to aid the caregiver in the monitoring of the health of the wearer. Certain attempts have been made in the art to include analysis of components of human waste, such as urine and feces, to provide indication of various specific health issues such as infections (e.g., urinary tract infections, etc.). For example, U.S. Pat. No. 5,468,236 issued to Everhart et al. on Nov. 21, 1995 discloses a disposable absorbent product that includes a chemically reactive means having an end point adapted to provide a visual indicator of the presence of a substance in mammalian bodily excrement. However, the prior art fails to provide the caregiver with a continuous monitoring for the early indication of the onset of a fever, often resulting in a delay in recognition of, and the ultimate diagnosis and treatment of, a wide variety of illnesses. Thus, it would be desirable to provide wearable articles with the capability to detect an elevated core body temperature in a wearer. It would also be desirable to provide absorbent articles with fever indicators that are capable of informing the wearer or caregiver of the wearer's temperature under certain circumstances. Further, it would be desirable for the fever indicators to provide quantitative or qualitative information to the user or caregiver.

SUMMARY OF THE INVENTION

The present invention is a wearable article comprising an outer cover adapted to fit about a portion of a wearer; and a fever indicator operatively associated with the outer cover, wherein the fever indicator provides a signal when a wearer's body temperature is above at least one predetermined threshold temperature, the fever indicator determining the wearer's body temperature from urine expelled from the wearer's body.

DETAILED DESCRIPTION OF THE INVENTION

The present invention is directed to a fever indicator that may be used in conjunction with a wearable article, including but not limited to disposable absorbent articles. As used herein, the term "wearable article" refers to articles adapted to be applied or affixed to, or otherwise associated with a portion of a wearer's anatomy for a certain period of time, and often during a wearer's normal activities. Wearable articles may encircle or at least partially enclose a portion of a wearer's body, such as in the case of belts, diapers, training pants, underwear, other garments, and the like. Such wearable articles may include elasticically extensible and/or fastening components to ensure a proper fit to the wearer and/or fastening components to provide for convenient application and removal of the article from the wearer by a caregiver. Alternatively, in addition to the above described features, at least a portion of the wearable article may be adhesively affixed to the skin of the wearer. In some embodiments, the wearable article may include a separate element, such as an insert, affixed to or associated with the wearable article. Although not limited to such embodiments, the present invention will generally be described below as associated with a disposable absorbent article.

As used herein, the term "absorbent article" refers to devices that absorb and contain body exudates and, more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles that are formed of separate parts united together to form a coordinated entity so that they do not require separate manipulative parts like a separate holder and/or liner. A preferred absorbent article embodiment of the present invention is the unitary disposable absorbent article, diaper 20, shown in FIG. 1. As used herein, the term "diaper" refers to an absorbent article generally worn by infants and incontinent persons about the lower torso. The present invention is also applicable to other wearable and absorbent articles such as incontinence briefs, incontinence undergarments, absorbent inserts, diaper holders and liners, feminine hygiene garments, bandages and the like.

Figure 1:
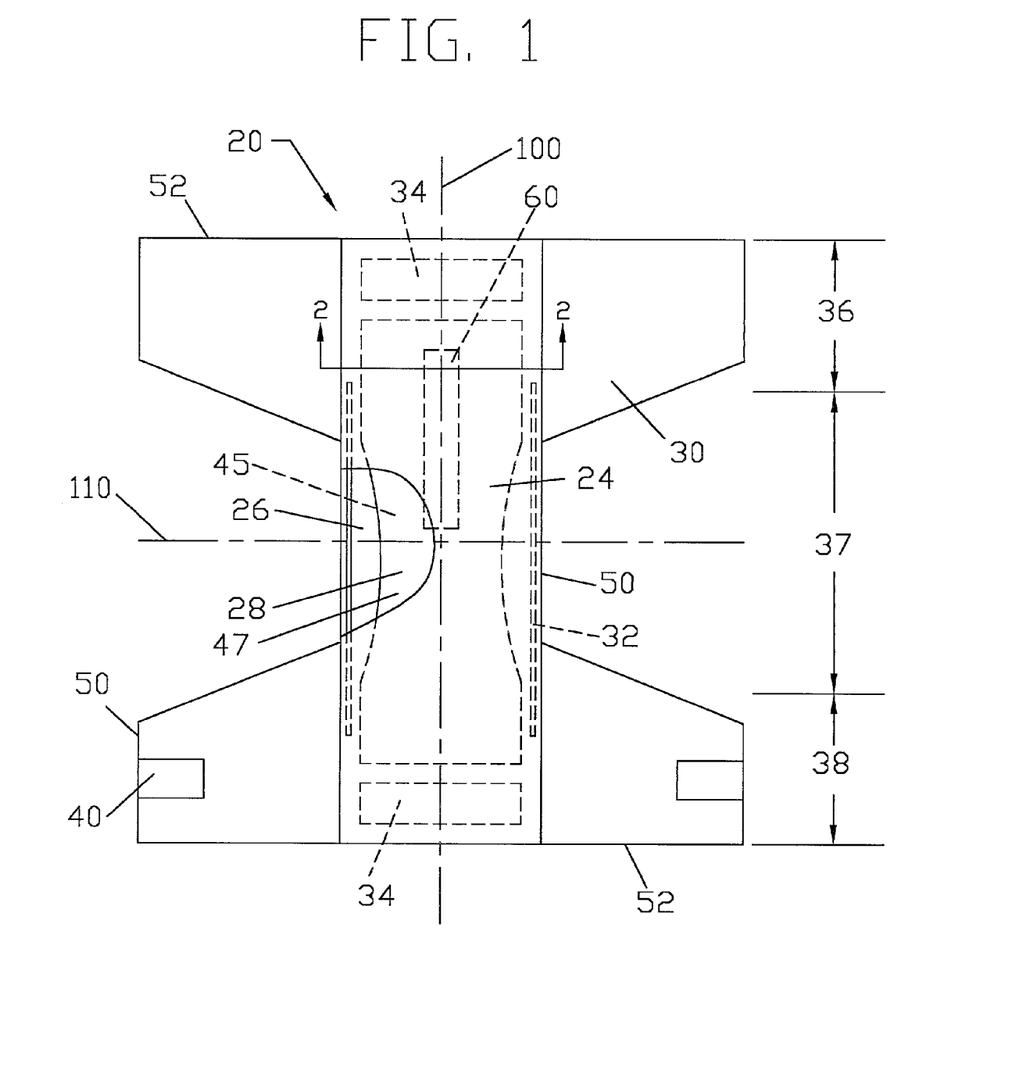
FIG. 1 is a plan view of a disposable diaper embodiment of the present invention with portions cut away to reveal underlying structure.

FIG. 1 is a plan view of the diaper 20 of the present invention in a flat-out state with portions of the structure being cut-away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26; an absorbent core 28 that is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The backsheet 26 is generally that portion of the diaper 20 positioned adjacent garment facing surface 45 of the absorbent core 28 that prevents the exudates absorbed and contained therein from soiling articles that may contact the diaper 20, such as bedsheets and undergarments. The topsheet 24 is preferably positioned adjacent body facing surface 47 of the absorbent core 28 and may be joined thereto and/or to the backsheet 26 by any attachment means known in the art. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. The topsheet 24 is preferably compliant, soft-feeling, and non-irritating to the wearer's skin. Further, at least a portion of the topsheet 24 is liquid pervious, permitting liquids to readily penetrate through its thickness.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

As noted above, the diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a surface fastener such as tape tabs, hook and loop fastening components and/or hermaphroditic fastening components, although any other known fastening means are generally acceptable. In alternative embodiments, opposing sides of the article may be seamed or welded to form a pant. This allows the article to be used as a pull-on type diaper, such as a training pant.

The article of the present invention further comprises a fever indicator 60 that provides a qualitative or quantitative visible, audible, or tactile signal of an elevated core body temperature of the wearer of the article. It has been shown in the medical literature that fresh urine temperature correlates well with core body temperature. Exemplary references in the medical literature include Ehrenkranz, J. R. L., et al, "A New Method of Measuring Body Temperature", *New Jersey Medicine,* Vol. 83, No. 2, Feb 1986, pp. 93–96, and Murray, H. W., et al, "Urinary Temperature: A Clue to Early Diagnosis of Factitious Fever", *Medical Intelligence,* Col. 296, No.1, 1977. Accordingly, the fever indicator of the present invention is preferably responsive to elevated urine temperatures.

In certain embodiments, the fever indicator 60 may provide a qualitative visual indication that the urine temperature, and therefore the core body temperature, is above a pre-defined threshold value. The threshold value is preferably set at a body temperature that would typically trigger a call or visit to a physician. For example, many physicians in the United States tell mothers of infants and young children that body temperatures above a specific level, generally in the range of about 100 degrees F. (about 37.8 degrees C.) to about 101 degrees F. (about 38.3 degrees C.), warrant contacting the doctor's office. Therefore, the fever indicator 60 may be designed, for example, to indicate to a mother, or other caregiver, that the temperature of the urine is at about 101 degrees F. (about 38.3 degrees C.) or above. In this event, the caregiver may choose to use a secondary temperature measurement tool (e.g., an infrared ear thermometer, oral thermometer, axillary thermometer, rectal thermometer, skin patch thermometer, etc.) to obtain a quantitative temperature measurement to provide to the doctor. In such a case, the fever indicator 60 functions as an "early warning" of a potential illness or infection and a signal to take secondary diagnostic action. The fever indicator 60 may provide a signal when the urine temperature is actually at or above the predefined threshold value. Alternatively, in certain embodiments the urine temperature may drop a known amount prior to contacting the fever indicator 60. In these embodiments, the fever indicator 60 may provide a signal at a urine temperature lower than, but correlated to, the predefined threshold value.

Figure 2:
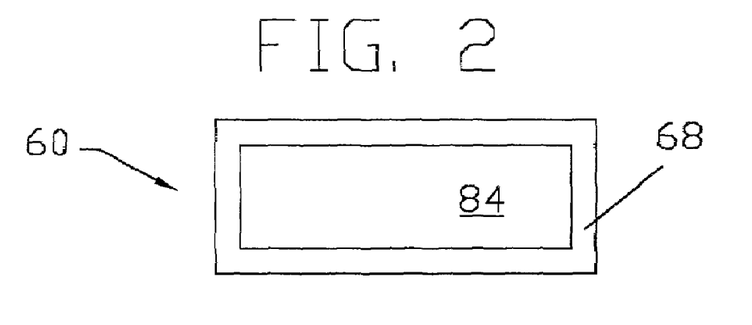
FIG. 2 shows a generic qualitative fever indicator.
Figure 3:
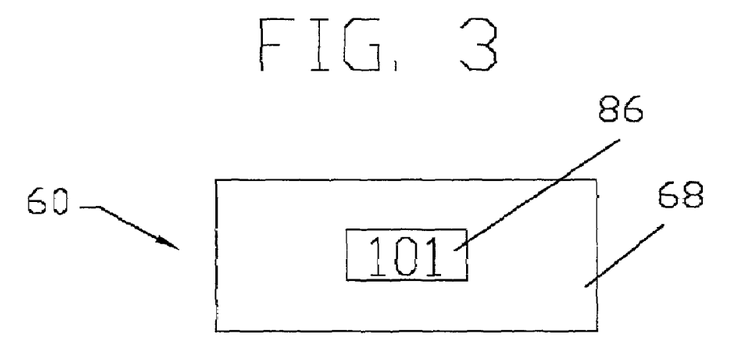
FIG. 3 shows a qualitative fever indicator having an alphanumeric signal.

Elevated body temperatures may be signaled to the caregiver via visible, audible, and/or tactile signals. In preferred embodiments of the present invention, a visual signal is provided to the caregiver by the fever indicator 60. Examples of visual signals include having a color or pattern appear, disappear, or change in color, shape, or design, or any combination thereof. The pattern may, for example, include one or more stripes, dots, alphanumeric characters, symbols, or pictures, or any combination thereof. FIG. 2 depicts an exemplary embodiment of a qualitative fever indicator wherein the smaller box 84 changes color when contacted by urine at or above the threshold temperature. FIG. 3 depicts another embodiment of a qualitative fever indicator wherein an alphanumeric designation 86 (the alphanumeric designation "101" is shown as an example) appears when contacted by urine at or above the threshold temperature, in this example 101 degrees F. (about 38.3 degrees C.).

In preferred embodiments, the fever indicator 60 should respond only to urine having a temperature above the predefined threshold value. Therefore, the fever indicator should respond only when the conditions of urine presence and a predefined temperature are met. Situations wherein the article is subjected to only one of these parameters should not result in an indication from the fever indicator 60. For example, the fever indicator 60 should not respond to high temperature in the absence of free water such as would be experienced in an unattended automobile on a hot sunny day. Further, the indicator should not respond to the presence of water in the absence of a temperature above the predefined threshold such as would be experienced when a healthy wearer having a normal body temperature urinates into the article.

Figure 4:
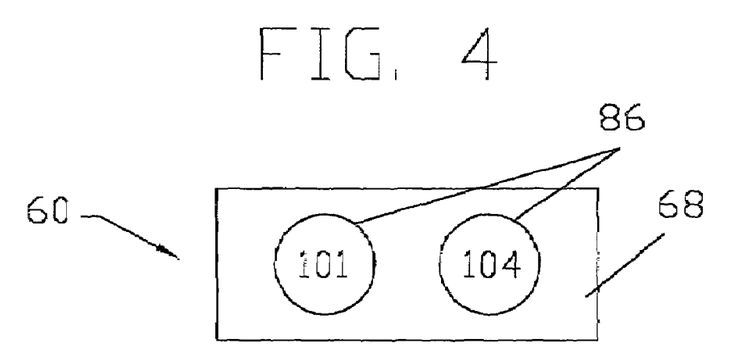
FIG. 4 shows a qualitative fever indicator having two temperature thresholds.
Figure 7:
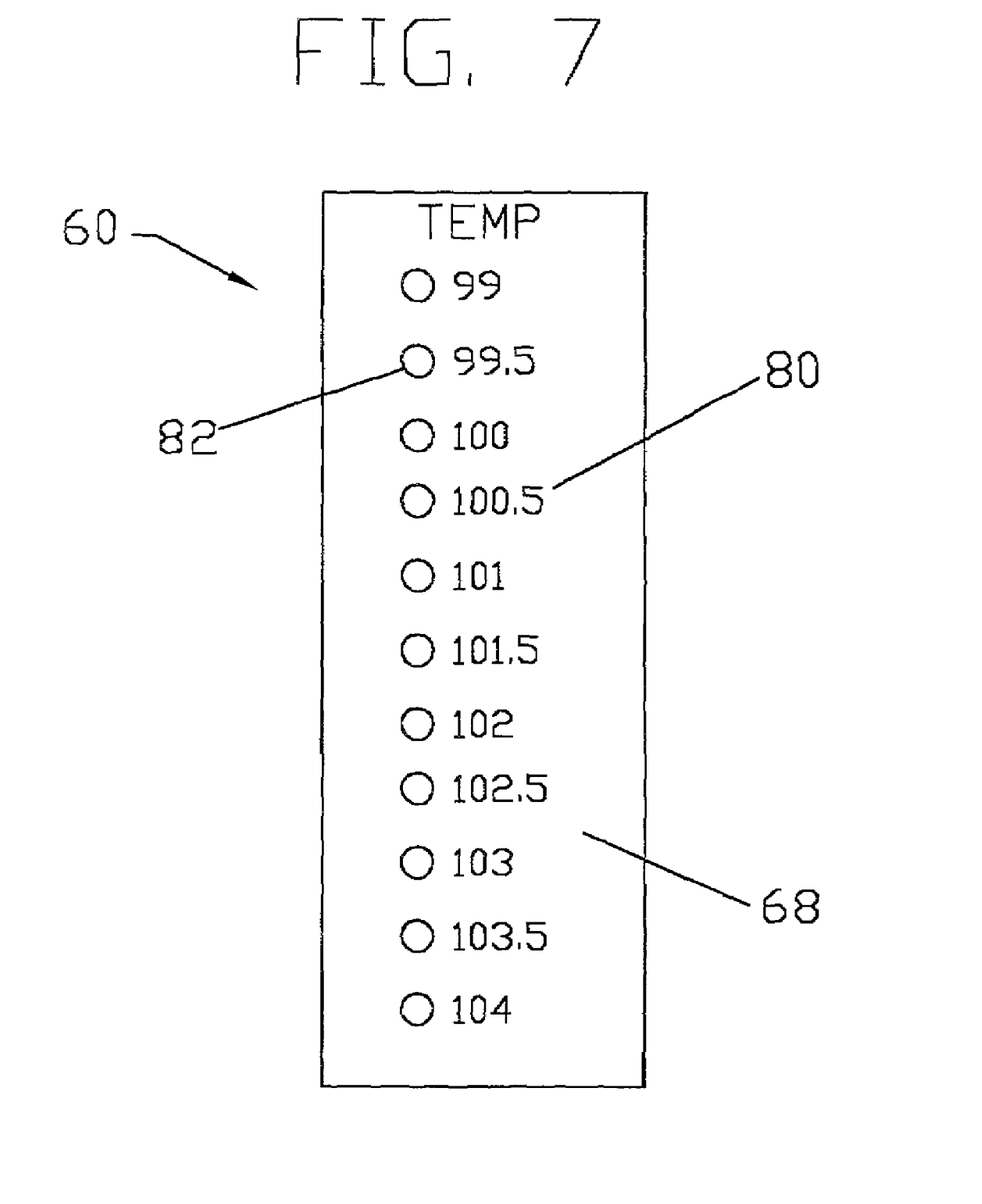
FIG. 7 shows a quantitative fever indicator having multiple temperature thresholds.

The fever indicator 60 may have the capability to indicate multiple temperature thresholds, providing a more quantitative indication of the severity of the fever. For example, the fever indicator 60 may include two temperature thresholds, indicating both moderate and severe fevers. In a non-limiting example, the fever indicator 60 may provide separate signals for fevers at 101 degrees F. (about 38.3 degrees C.) and 104 degrees F. (about 40.0 degrees C.), as indicated by the alphanumerics 86 shown in FIG. 4. Alternatively, the fever indicator 60 may include a multiplicity of temperature thresholds, each providing a separate signal, at regular intervals through the temperature region of interest. For example, the fever indicator 60 may have temperature thresholds at intervals of 0.5 degrees F. (about 0.28 C degrees) through the range of 100 degrees F. (about 37.8 degrees C.) to 104 degrees F. (about 40.0 degrees C.). In embodiments having more than one temperature threshold, the fever indicator 60 may provide different visual signals for each threshold (i.e., a different color, symbol, alphanumeric symbol, shape, etc., or combination thereof). In certain embodiments, each threshold may comprise a simple signal (e.g., a colored dot 82) next to an indicium 80 on the carrier element 68, one example of which is shown in FIG. 7. The temperature indicating systems described in U.S. Pat. Nos. 5,094,545; 4,345,470; 4,564,299; or 5,222,809, all of which are hereby incorporated by reference herein, may be suitable for use in the article of the present invention.

Regardless of the number of temperature thresholds and/or the nature of the signal, the fever indicator 60 preferably provides a signal sufficiently durable so as to be readable at any time between the triggering urination event and the removal of the article. Typically, the signal should be visible for at least about 1 hour after contact with urine having a temperature above the predefined threshold value. Preferably, the signal should be visible for at least about 2 hours, and more preferably at least about 12 hours, after contact with urine having a temperature above the predefined threshold value.

Upon contact with urine having an elevated temperature, i.e., urine from a wearer having a core body temperature above the predefined threshold value, the fever indicator 60 should respond, i.e., provide a visible signal, prior to the time when the urine has cooled to a temperature below which the urine temperature is indistinguishable from the temperature of urine from a wearer having a normal core body temperature. Typically, the fever indicator 60 provides a signal within about 5 minutes of contacting urine having a temperature above the predefined threshold value. Preferably, the fever indicator 60 provides a signal within about 1 minute, and more preferably within about 20 seconds, of contacting urine having a temperature above the predefined threshold value A qualitative visual fever indicator 60 may indicate an elevated body temperature by having a color or pattern appear, disappear, or change in color, shape, or design, or any combination thereof. The pattern may, for example, include one or more stripes, dots, alphanumeric characters, symbols, or pictures, or any combination thereof. The fever indicator 60 may be visible from inside the article or outside the article and may be affixed to any component of the article. For example, the fever indicator 60 may be affixed to the topsheet 24, the absorbent material 28, or the backsheet 26. In certain preferred embodiments, the fever indicator 60 is positioned directly beneath the topsheet 24 and is visible after the article is at least partially removed from the wearer. In certain alternative embodiments, the fever indicator 60 may be positioned on the inside of an article, such as on the inside of the backsheet, such that it can be seen through at least a portion of the outer cover. In yet other embodiments, the fever indicator 60 may be disposed on the article in such a way that a patch or portion of the article can be pulled away, permanently or temporarily, such that the indicator is visible without the article being removed from the wearer. In yet other embodiments, the fever indicator 60 may comprise a separate element applied to the article by the caregiver, such as a diaper insert or other carrier element affixed to the topsheet 24 (e.g., via adhesive, a mechanical fastener, friction, etc.) by the caregiver prior to applying the article to the wearer.

Figure 5:
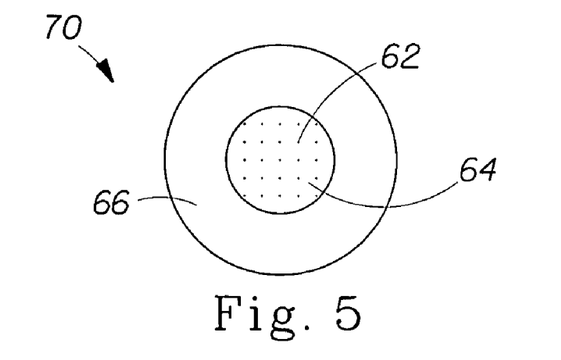
FIG. 5 is a cross-sectional view of a particulate form of a fever indicator.

The fever indicator 60 generally includes a fever indicating composition 70 or element. The fever indicating composition may be in any physical form, including particles and films. Certain preferred fever indicating compositions may include an indicating component, a temperature sensitive component and a urine sensitive component that function together to provide the caregiver a visual indication of the wearer's elevated body temperature. In one exemplary embodiment, as shown in FIG. 5, the fever indicating composition 70 includes an indicating composition 62 in the form of particles suspended in a temperature sensitive component 64 surrounded by a urine sensitive component 66. The indicating component 62, temperature sensitive component 64 and urine sensitive component 66 may each be separate and different components or one element or material may perform more than one of these functions.

The temperature sensitive component 64 may include a composition having a melting or softening point at the predefined threshold value. An exemplary temperature sensitive component is 1-tetradecanol, glycerol diacetate, or myristyl alcohol, which has a melting point of about 38 degrees C. Other nonlimiting exemplary temperature sensitive compositions may include methyl stearate and teppineol. Alternatively, certain waxes and mixtures of other materials may be adapted for use as temperature sensitive components of a fever indicator.

The urine sensitive component 66 preferably changes properties in the presence of urine or is at least partially permeable by urine. For example, the urine sensitive component 66 may dissolve or become more permeable in the presence of urine. The urine sensitive component 66 may sense, or respond to, any of the components or properties of urine, including water, pH. enzymes, urea, etc. Exemplary materials suitable for use in the urine sensitive component 66 include starches and sugars, polyvinyl alcohol (in situ formed films and pre-manufactured films), gelatins, and other water or pH soluble films or materials. Other suitable materials include wetness or urine indicating compositions as known in the art, such as hoc melt wetness indicators, water soluble dye systems, etc., including those described in U.S. Pat. Nos. 4,022,211; 4,743,238; 5,066,711; 5,342,861; 4,681,576; 5,035,691; 4,231,370; 4,895,567; and 6,075,178; incorporated herein by reference. Additionally, novel urine indicating compositions, such as those described in U.S. Pat. No. 6,772,708 for a Wetness Indicator Having Improved Colorant Retention, issued on 10 Aug. 2004, may be employed as the urine sensitive component 66. For example, the urine sensitive component may comprise stearyl alcohol, microcrystalline waxes, etholxylated alcohols, cationic quaternary amines, or mixtures thereof, and an indicating component, such as a pH indicator. In certain alternate embodiments, the urine sensitive component may comprise a material or composite having different optical properties (e.g., contrast) in the wet state versus the dry state, such as films or tissues having patterns printed in permanent ink which appear, when viewed through the backsheet, darker when wetted.

The indicating component 62 of the urine indicator 60 may comprise a colorant, dye, or indicator that changes appearance (e.g., color) upon contact with urine at a temperature above a certain threshold. Non-limiting exemplary embodiments of the indicating component include food grade dyes such as FD&C No.1 Blue, and pH indicators such as bromocresol green and bromophenol blue.

In certain alternate embodiments wherein the fever indicator is applied as a stripe or layer to a flexible substrate, such as a film, the previously described glycerol diacetate may act as a plasticizer to prevent the fever indicator, or any component thereof, from cracking under mechanical stress and leading to false positives or negatives. In the context of a fever indicator, a plasticizer may comprise any compound or composition that is at least partially soluble or miscible in the temperature sensitive component and/or the urine indicating component and that reduces the tendency of the component to form crystallized regions, thereby reducing the glass transition temperature of the component and increasing its flexibility in the temperature range in which the article is expected to be used. Additional non-limiting examples of suitable plasticizers include polyhydroxy compounds such as glycerol and polyethylene glycols, microcrystalline waxes, isoparaffins, querbert alcohols, branched esters, branched alcohols, and other compounds such as those described above.

The fever indicator 60, or any of the components thereof, may be applied to a substrate, such as the article or any component thereof or to a carrier element, via any means known in the art. For fever indicators, or components thereof, that are applied in a liquid or molten state to the substrate in a continuous or intermittent mode, or in patterns, suitable exemplary processes include slot coating, gravure printing, inkjet printing, spraying, screening, and the like. The indicator may also be applied to the substrate or article in a solid form, such as films, webs, fibers, or particles via continuous unwind processes, cut & slip processes, air deposition, and the like, and may be joined to the substrate via physical entanglement, entrapment, adhesives or any other means as known in the art.

In certain preferred embodiments, the fever indicator 60 may comprise a wetness indicator, such as those described herein, disposed as a thin layer in a pattern or stripe format on the inside of the backsheet of a disposable article and covered with a thin layer of a temperature sensitive component. In these embodiments, the layer of temperature sensitive component should cover the wetness indicator without interruption. Preferably the layer of temperature sensitive component extends past the periphery of the wetness indicator, at least in any region of the fever indicator 60 that may contact urine while the article is being worn by a wearer, in order to prevent "false positive" signals by the fever indicator 60.

Figure 6:
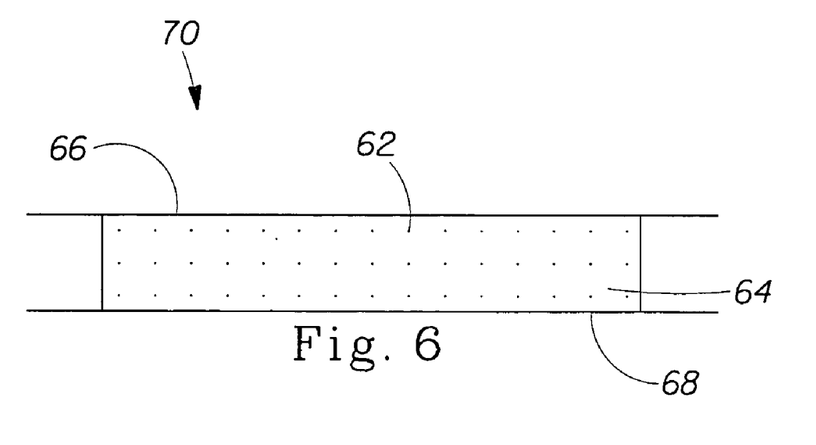
FIG. 6 is a cross-sectional view of a layered form of a fever indicator.

As noted above and shown in FIG. 6, the fever indicator 60 may be disposed on or in a substrate, or carrier element 68. The carrier element 68 may comprise a web-like component such as a film, woven or nonwoven material, foam, scrim, or cellulosic material, to which the fever indicating composition or element is applied or affixed. Alternately, the carrier 68 may enclose or encapsulate a fever indicating composition to prevent its migration or loss within the article before or during use. In these embodiments, the carrier 68 may comprise one layer folded back upon itself or may comprise a multiplicity of layers. If more than one layer is employed, the various layers may have different properties or comprise different materials. For example, a fever indicating composition 70 may be disposed between a permeable top (i.e., wearer-facing) layer and an impermeable bottom layer. In certain embodiments, the top layer may alternatively comprise a selectively permeable layer, a dissolving layer, a pH sensitive layer, or a coating. The carrier 68 may be flexible or may be relatively rigid. In certain embodiments, the fever indicator 60 may be detachable from the article.

While the fever indicator 60 may be located at any point in the article likely to be contacted by urine, the fever indicator 60 is preferably located in the portion of the article coordinated with the urine loading point (i.e., the location in which the urine typically insults the article, such as in the vicinity of the longitudinal centerline of the article in the crotch region of the article). Generally, the urine temperature is easily measured at or near the topsheet of the article (e.g., on the wearer facing side or underside of the topsheet) in the vast majority of urine loading occurrences. In the most highly preferred embodiments of the present invention, the fever indicator 60 is affixed to the topsheet or any other component of the article located above the absorbent core, including the wearer facing surface of the absorbent core. In many occurrences where the fever indicator is located at or near the inner surface of the backsheet, or on any carrier disposed on the underside of an absorbent core, the fever indicator may be limited to detecting an elevated wine temperature for only the initial urine loading event since relatively large quantities of existing fluid held in the absorbent core may act as a heat sink and prematurely cool subsequent urine voidings below the predefined temperature threshold. Additionally, a fever indicator 60 located between the absorbent core and the backsheet of an article may require higher urine temperatures, greater urination event volumes, and/or slower urine loading rates (i.e., to ensure maximum absorption in the immediate vicinity of the urination point) to reliably detect the presence of an elevated core body temperature.

EXEMPLARY EMBODIMENTS

Example 1

A qualitative fever indicator having a single temperature threshold at approximately 101 degrees F. suitable for use in a disposable absorbent article may be constructed as follows:

1. 0.02 grams of a food grade dye that displays a noticeable color when dissolved in water is dispersed in 100 grams of molten 1-tetradecanol. Preferably, the dye has a blue, green, or purple color when dissolved in water. An example of a suitable blue dye is FD&C No. 1 Blue, which is principally the disodium salt of ethyl[4-[-[ethyl(m-sulfobenzyl)amino]-α-(o-sulphophenyl)benzylidene]-2,5-cyclohexdien-1-ylidene](m-sulphobenzyl) ammonium hydroxide inner salt. This compound is commonly designated CAS#2650-18-2. The CAS# refers to the unique numerical designation assigned to a chemical by the Chemical Abstracts Service (CAS) of Columbus, Ohio, USA, which is a division of the American Chemical Society of Washington, D.C. USA.
2. The molten tetradecanol is cooled and formed into small particles, preferably smaller than 1 mm in largest dimension. Alternatively, the mixture may be spray-dried to form roughly spherical particles. Preferred particle sizes are approximately 200 microns.
3. The particles from step 2 are coated, e.g., in a fluidized bed, with additional molten 1-tetradecanol and cooled. The thickness of the coating may vary from several microns to about 1 mm.
4. The particles from step 2 are coated with a polyvinyl alcohol film coating.
5. The particles are encapsulated between a layer of nonwoven and a layer of polypropylene film, each having the dimensions of 1 cm by 4 cm. The layers are thermomechanically, adhesively, ultrasonically or otherwise bonded together.
6. The composite from step 4 is affixed to the underside of a diaper topsheet in the crotch region via hot melt adhesive.

Example 2

A qualitative fever indicator having a single temperature threshold at approximately 101 degrees F. suitable for use in a disposable absorbent article may be constructed as follows:

1. 0.2 grams of bromophenol blue pH indicator is dispersed in 100 grams of molten 1-tetradecanol.
2. The mixture from step 1 is applied in a molten form in an 0.5 by 3 cm stripe at a basis weight of 25 grams per square meter to a piece of polypropylene film. The mixture is allowed to cool and harden.
3. A layer of polyvinyl alcohol film is applied over the strip from step 2.
4. The composite from step 4 is affixed to the underside of a diaper topsheet in the crotch region of the diaper via a hot melt adhesive.

Example 3

A fever indicator having multiple temperature thresholds at approximately 101 and 104 degrees F. suitable for use in a disposable absorbent article may be constructed as follows:

1. 0.2 grams of bromophenol blue pH indicator is dispersed in 100 grams of molten 1-tetradecanol to form mixture A.
2. 0.2 grams of bromophenol blue pH indicator is dispersed in 100 grams of molten glycerol diacetate to form mixture B.
3. Mixture A is applied in a molten form in an 0.5 cm diameter dot at a basis weight of 25 grams per square meter to a piece of polypropylene film having the dimensions of about 2 cm by about 5 cm. The mixture is allowed to cool and harden.
4. Mixture B is applied in a molten form in an 0.5 cm diameter dot at a basis weight of 25 grams per square meter to the same piece polypropylene film. A 1 cm gap is left between the dots formed with mixtures A and B. The mixture is allowed to cool and harden.
5. Dots of molten 1-tetradecanol and glycerol diacetate having diameters of 1.0 cm and a basis weight of 25 gsm are applied directly over the dots A and B, respectively, from steps 3 and 4 and allowed to cool and harden.
6. A layer of polyvinyl alcohol film is applied over the dots from step 5.
7. The composite from step 4 is affixed to the underside of a diaper topsheet in the crotch region of the diaper via a hot melt adhesive.

Example 4

A quantitative fever indicator having multiple temperature thresholds suitable for use in a disposable absorbent article, and integral with the article, may be constructed as follows:

A carrier having a multiplicity of depressions or "wells" is provided. Each well is at least partially filled with a different temperature indicating mixture, each mixture adapted to change color at a different threshold temperature. The temperature indicating mixtures preferably change color upon the transition from a solid to a liquid state that occurs at the threshold temperature. An exemplary mixture may be produced by dissolving 5.0 weight percent of a dye such as pinacyanol iodide in a 75:25 ratio mixture of ortho-bromonitro-benzene and ortho-chloronitrobenzene at about 50 degrees C., and subsequently allowing the mixture to cool. This mixture has a temperature threshold of about 100.5 degrees F. (about 38.04 degrees C.). Additional mixtures may be similarly prepared having different temperature thresholds, providing the basis for a series of discrete increments in temperatures change thresholds, e.g., 0.5 degree F. increments in as shown in FIG. 7. Further examples of mixtures having different temperature thresholds are described in U.S. Pat. No. 4,232,552. The fever indicator may then be affixed to the underside of the topsheet of the article with the wells facing the wearer.

Example 5

A qualitative fever indicator having a single temperature threshold suitable for use in a disposable absorbent article may be constructed as follows:

1. The inner surface of a 1.0 mil thick polypropylene film is coated with a film of a molten wetness indicating adhesive having a basis weight 26 grams per square meter and width of 5 millimeters. Any known wetness indicating adhesive adapted to provide a color change when contacted by urine, including those described herein, is suitable, especially those adhesives comprising a pH indicator, such as bromocresol green and bromophenol blue, having a color transition in the range of about pH 3 to about pH 6. Examples of suitable commercially available wetness indicating adhesives include FINDLEY™ 9219-01, 9052, and 9133-05 adhesives available from Bostik-Findley of Middleton, Mass., U.S.A.

2. After the film from step 1 has solidified, it is completely covered by a layer of 1-tetradecanol. This 1-tetradecanol layer has a basis weight of between 26 to 39 grams per square meter, and a width of 15 millimeters. The 1-tetradecanol layer is oriented such that its width extends 5 mm on either side of the width of the wetness indicating adhesive layer.

3. The resultant composite, or a portion thereof, maybe affixed to the inner surface of a disposable diaper topsheet or backsheet.

Example 6

A qualitative fever indicator having a single temperature threshold suitable for use in a disposable absorbent article may be constructed as follows:

1. A urine indicating composition is prepared according to the formula and procedure described below:

| Ingredient | Grams |
| --- | --- |
| Stearyl Alcohol | 49.8 |
| Microcrystalline Wax | 10.0 |
| Stearyl Phosphate | 10.0 |
| Dimethyl(2-ethylhexylhydrogenated tallowalkyl)ammonium methyl sulfate | 10.0 |
| Bromocresol Green (powdered acid form) | 0.2 |
| C20–C40 Pareth-40 nonionic surfactant | 20.0 |

This urine indicating composition is made by first weighing out the correct amounts of stearyl alcohol, microcrystalline wax, and stearyl phosphate into a stainless steel container. The stearyl alcohol should be a white waxy solid with a purity of at least 97% and no more than 2% of arachidyl alcohol, and have a melting point in the range of about 56° C. to about 60° C. The product designated CO1897 stearyl alcohol available from The Procter & Gamble Company of Cincinnati, Ohio, U.S.A., is a current example of a suitable material. The microcrystalline wax should be a high molecular weight petroleum based wax consisting of saturated branched and cyclic non-polar hydrocarbons and possessing a melting point in the range of about 60° C. to about 95° C. The product designated MULTIWAX™ W-835 available from the Crompton Corporation of Petrolia, Pa., U.S.A. is an example of a suitable microcrystalline wax. This mixture is heated and mixed at a temperature in the range of about 100° C. to about 110° C. until the mixture is a clear, transparent and colorless molten mixture. The dimethyl(2-ethylhexylhydrogenated tallowalkyl)ammonium methyl sulfate is then added to the above molten mixture and heated at a temperature in the range of about 100° C. to about 110° C. for 10 minutes. The dimethyl(2-ethylhexylhydrogenated tallowalkyl)ammonium methyl sulfate should have a quaternary salt content of 81.5–84.5%, possess a free amine and free amine salt impurity content of no more than 4%, and have an HLB of 17–18. The product designated ARQUAD™ HTL8(W)-MS available from Akzo-Nobel of Chicago, Ill., U.S.A. is a good example of a dialkyldimethyl quaternary ammonium salt currently meeting these requirements. To this mixture, the bromocresol green pH indicator is added. The resultant mixture is heated while mixing at a temperature in the range of about 100° C. to about 110° C. for 20 mixtures. Finally, to this mixture, C20–C40 Pareth-40 surfactant is added, the surfactant having been preheated to a temperature in the range of about 100° C. to about 110° C. The C20C40 Pareth-40 surfact should have molecular weight ($M_n$) between about 2200 and about 2400, an ethylene oxide content between in the range of about 75% to about 85%, an HLB of approximately 16, and a melting point in the range of about 80° C. to about 94° C. The product designated PERFORMATHOX™ 480 available from New Phase Technologies of Sugar Land, Tex., U.S.A is an example of a suitable C20–C40 Pareth-40 meeting these requirements. The entire composition is subsequently heated at a temperature in the range of about 100° C. to about 110° C. until it is clear, transparent and yellow-orange in color.

2. A 5 mm wide stripe of the composition from step 1 above is applied to the inner surface of a 1.0 mil thick polypropylene film is coated with at a basis weight of 26 grams per square meter and width of 5 millimeters.

3. After the film from step 2 has solidified, it is completely covered by a continuous layer of 1-tetradecanol. This 1-tetradecanol layer has a basis weight of between 26 to 39 grams per square meter, and a width of 15 millimeters. The 1-tetradecanol layer is oriented such that its width extends 5 mm on either side of the width of the urine indicating composition layer.

What is claimed is:

1. A wearable article comprising an outer cover adapted to fit about a portion of a wearer and a fever indicator affixed to the outer cover,
   the fever indicator comprising a temperature sensitive component and an indicating component,
   the temperature sensitive component covering the indicating component and thereby preventing wetting of the indicating component prior to melting at a predetermined threshold temperature and thereby allowing wetting of the indicating component by urine expelled from the wearer,
   the indicating component changing in appearance when wetted and thereby providing a visible signal.

2. The wearable article of claim 1 wherein the fever indicator provides a qualitative indication of a fever.

3. The wearable article of claim 2 wherein the fever indicator comprises a urine sensitive component.

4. The wearable article of claim 3 wherein the urine sensitive component dissolves upon contact with urine.

5. The wearable article of claim 1 wherein the visible signal is a color change.

6. The wearable article of claim 1 wherein the fever indicator provides a quantitative indication of a fever.

7. The wearable article of claim 1 wherein the fever indicator is disposed on a carrier element.

8. The wearable article of claim 1 wherein the fever indicator comprises a plasticizer.

9. A disposable absorbent article for receiving and containing bodily exudates, the disposable absorbent article comprising:
   an outer cover adapted to fit about a portion of a wearer;
   a fluid permeable topsheet;
   an absorbent structure disposed adjacent at least a portion of the outer cover; and
   a fever indicator affixed to a component of the disposable absorbent article, the fever indicator comprising a temperature sensitive component and an indicating component, the temperature sensitive component covering the indicating component and thereby preventing wetting of the indicating component prior to melting at a predetermined threshold temperature and thereby allowing wetting of the indicating component by urine expelled from the wearer, the indicating component changing in appearance when wetted and thereby providing a visible signal.

10. The disposable absorbent article of claim 9 wherein the fever indicator is affixed to the topsheet.

11. The disposable absorbent article of claim 10 wherein the fever indicator is detachable from the topsheet.

12. The disposable absorbent article of claim 9 wherein the fever indicator provides a qualitative or quantitative indication of a fever.

13. The disposable absorbent article of claim 9 wherein the visible signal is a color change.

14. The disposable absorbent article of claim 9 wherein the fever indicator comprises a urine sensitive component.

15. The disposable absorbent article of claim 9 wherein the fever indicator is disposed on a carrier element.

16. The disposable absorbent article of claim 9 wherein the fever indicator comprises a plasticizer.

17. An insert for use with a wearable article, the insert comprising a fever indicator comprising a temperature sensitive component and an indicating component, the temperature sensitive component covering the indicating component and thereby preventing wetting of the indicating component prior to melting at a predetermined threshold temperature and thereby allowing wetting of the indicating component by urine expelled from a wearer, the indicating component changing in appearance when wetted and thereby providing a visible signal.

18. The insert of claim 17 wherein the fever indicator further comprises a urine sensitive component.

* * * * *

UNITED STATES PATENT AND TRADEMARK OFFICE
CERTIFICATE OF CORRECTION

PATENT NO. : 7,002,054 B2
DATED : February 21, 2006
INVENTOR(S) : Allen et al.

It is certified that error appears in the above-identified patent and that said Letters Patent is hereby corrected as shown below:

Column 7,
Line 7, delete "pH." and insert -- pH, --.
Line 13, delete "hoc" and insert -- hot --.

Column 8,
Line 56, delete "wine" and insert -- urine --.

Column 9,
Line 14, delete "ethyl[4-[-" and insert -- ethyl[4-[p- --.

Column 11,
Line 7, delete "C20C40" and insert -- C20-C40 -- and delete "surfact" and insert -- surfactant --.

Signed and Sealed this

Sixteenth Day of May, 2006

JON W. DUDAS
*Director of the United States Patent and Trademark Office*